US00PP16533P2

(12) United States Plant Patent
Trees

(10) Patent No.: US PP16,533 P2
(45) Date of Patent: May 16, 2006

(54) ***GERANIUM* PLANT NAMED 'BALFANIMFRO'**

(50) Latin Name: *Pelargonium×hortorum*
Varietal Denomination: Balfanimfro

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 114 days.

(21) Appl. No.: 11/011,317

(22) Filed: Dec. 13, 2004

(51) Int. Cl.
*A01H 5/00* (2006.01)

(52) U.S. Cl. ..... Plt./327
(58) Field of Classification Search ..... Plt./327
See application file for complete search history.

(56) References Cited

U.S. PATENT DOCUMENTS

PP10,349 P * 4/1998 Hanes ..... Plt./328
PP11,767 P2 * 2/2001 Trees ..... Plt./328
PP12,364 P2 * 1/2002 Utecht ..... Plt./329

OTHER PUBLICATIONS

UPOV ROM GTITM Computer Database, GTI Jouve Retrieval Software 2005/02 Citation for 'Balfanimfro'.*

* cited by examiner

*Primary Examiner*—Kent Bell
*Assistant Examiner*—W. C. Haas
(74) *Attorney, Agent, or Firm*—Wood, Phillips, Katz, Clark & Mortimer

(57) ABSTRACT

A new and distinct cultivar of *Geranium* plant named 'Balfanimfro' characterized by its semi-double salmon-colored flowers, dark green-colored foliage, and vigorous, upright and mounded growth habit.

1 Drawing Sheet

Latin name of genus and species of plant claimed: *Pelargonium×hortorum.*
Variety denomination: 'Balfanimfro'.

BACKGROUND OF THE INVENTION

The present invention relates to a new and distinct cultivar of *Geranium* plant botanically known as *Pelargonium× hortorum* and hereinafter referred to by the cultivar name 'Balfanimfro'.

The new cultivar originated in a controlled breeding program in Arroyo Grande, Calif., during March 1999. The objective of the breeding program was the development of *Geranium* cultivars with a vigorous, upright and mounded growth habit, dark green-colored foliage, and new and unique flower color.

The female (seed) parent of the new cultivar was 'Fissil', U.S. Plant Pat. No. 12,364, characterized by its single magenta-colored flowers, medium green-colored foliage and medium growth habit. The male (pollen) parent of the new cultivar was 'Clips Light Lav', U.S. Plant Pat. No. 10,349, characterized by its semi-double light lavender-colored flowers and dark green-colored foliage. The new *Geranium* was discovered and selected by the inventor as a single flowering plant within the progeny of the above stated cross-pollination during February 2000 at Arroyo Grande, Calif.

Asexual reproduction of the new cultivar by terminal stem cuttings taken since February 2000 at Arroyo Grande, Calif. and West Chicago, Ill., has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Balfanimro' as a new and distinct cultivar of *Geranium* plant:

1. Semi-double salmon-colored flowers.
2. Dark green-colored foliage.
3. Vigorous, upright and mounded growth habit.

Plants of the new cultivar differ from plants of the female parent primarily in growth habit and flower form and from plants of the male parent primarily in flower color.

Of the many commercially available *Geranium* cultivars known to the inventor, the most similar in comparison to the new cultivar is 'Balfanfaro', U.S. Plant Pat. No. 11,767. However, in side by side comparisons, plants of the new cultivar differ from plants of 'Balfanfaro' in the following characteristics:

1. Plants of the new cultivar exhibit darker flower color than plants of 'Balfanfaro'.
2. Plants of the new cultivar exhibit a more distinct leaf zonation than plants of 'Balfanfaro'.
3. Plants of the new cultivar have smaller umbels than plants of 'Balfanfaro'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balfanimfro'. The plants were grown for 8 weeks in a greenhouse at West Chicago, Ill.

DETAILED BOTANICAL DESCRIPTION

Figure 1:
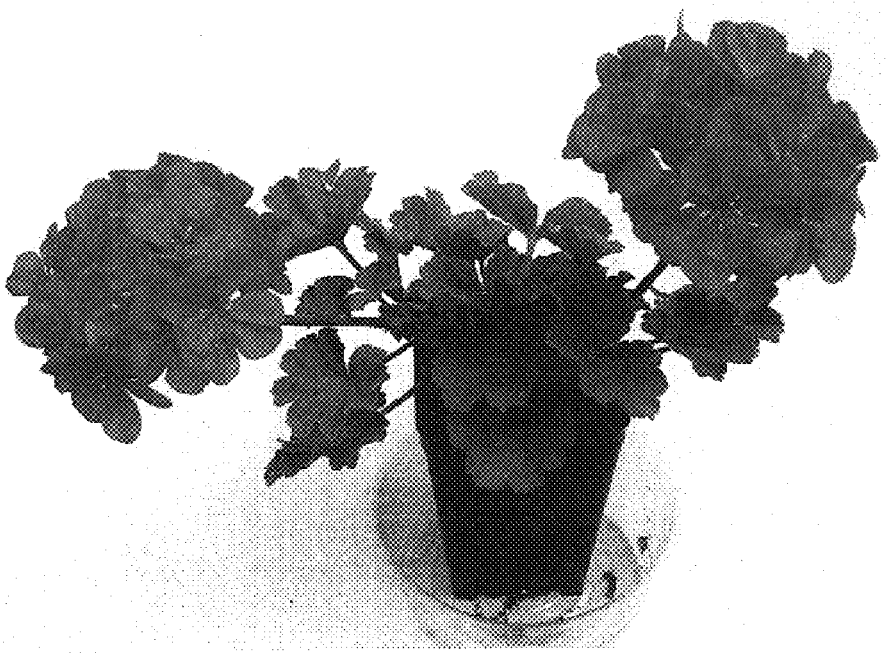
FIG. 1 illustrates a side view of the overall growth and flowering habit of 'Balfanimfro'.
Figure 2:
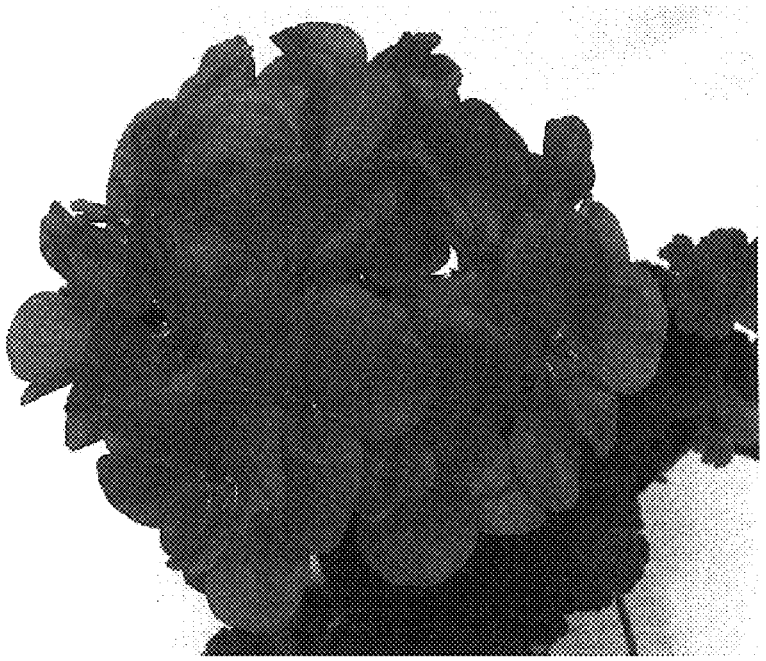
FIG. 2 illustrates a close-up view of a single umbel of 'Balfanimfro'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Oct. 8, 2004 between 10:00 and 11:45 a.m. under natural light conditions, in West Chicago, Ill.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 8 weeks utilizing a soilless growth medium. Greenhouse temperatures were maintained at approximately 65° F. to 70° F. (18° C. to 21° C.) during the day and approximately 60° F. to 65° F. (15° C. to 18° C.) during the night. Greenhouse light levels of 4,000–6,000 footcandles were maintained during the day. Plants were pinched at three weeks after the planting of a rooted cutting.

Botanical classification: *Pelargonium×hortorum* cultivar 'Balfanimfro'.

Parentage:

*Female parent.*—'Fissil', U.S. Plant Pat. No. 12,364.

*Male parent.*—'Clips Light Lav', U.S. Plant Pat. No. 10,349.

Propagation:

*Type cutting.*—Terminal stem.

*Time to initiate roots.*—Approximately 10 to 14 days.

*Time to produce a rooted cutting.*—Approximately 21 to 28 days.

*Root description.*—Fibrous.

*Rooting habit.*—Freely branching.

Plant description:

*Crop time.*—Approximately 8 to 9 weeks from a rooted cutting to finish in a 10 cm pot.

*Growth habit and general appearance.*—Vigorous, upright and mounded.

*Height from soil level to top of plant plane.*—Approximately 18.9 cm.

*Width/area of spread.*—Approximately 26.9 cm.

*Branching habit.*—Freely basal branching. Approximately 2 branches per plant.

*Branch description.*—Strength: Strong. Length: Approximately 6.1 cm. Diameter: Approximately 6.6 mm. Texture: Dense, short, soft. Color: closest to 144B. Internode length at center of branch: Approximately 1.4 cm.

*Foliage description.*—Number of leaves per lateral branch: Approximately 11. Fragrance: None. Form: Mature foliage is simple. Arrangement: Opposite. Shape: Reniform. Margin: Crenate. Apex: Rounded. Base: Cordate. Venation pattern: Palmate. Texture of upper surface: Densely pubescent. Texture of lower surface: Moderately pubescent with dense pubescence along veins. Color of upper surface of mature foliage: 137A with veins of 144A. Color of lower surface of mature foliage: 146A with veins of 144A. Length of mature leaf: Approximately 4.7 cm. Width of mature leaf: Approximately 5.3 cm. Petiole length: Approximately 4.9 cm. Petiole diameter: Approximately 2.8 mm. Petiole Texture: Pubescent on both upper and lower surface. Petiole color: 144A with glands of 28B.

Flowering description:

*Outdoor flowering habit.*—'Balfanimfro' is freely flowering under outdoor growing conditions with substantially continuous blooming from spring through autumn and year round in greenhouse environment.

*Time to first flower.*—Approximately 8 weeks after planting of rooted cutting.

*Lastingness of individual bloom.*—Approximately 5 to 7 days.

Inflorescence description:

*Type.*—Hemispherical umbel. Position: Above foliage. Number of open umbels at any one time: 3. Number of developing umbels at any one time: 2. Diameter of fully open umbel: Approximately 9.9 cm. Height/depth of fully open umbel: Approximately 6 cm. Number of flowers per umbel: Approximately 17.

*Peduncle.*—Strong, erect. Length: Approximately 17.5 cm. Diameter: Approximately 3.3 mm. Texture: Dense, short, soft. Color: 144A.

Flower description:

*Bud rate of opening.*—Generally takes from 3 to 5 days for buds to progress from first color to fully open floret.

*Bud just before opening.*—Shape: Elliptic. Length: Approximately 1.3 cm. Diameter: Approximately 8 mm. Texture: Dense. Petal color: Betweem 52A and 52B. Sepal color: 144A.

*Corolla.*—Form: Semi-double. Shape: Round, slightly cupped. Diameter/Width: Approximately 4.3 cm. Depth: Approximately 1.9 cm. Fragrance: None. Persistent.

*Petals/petaloids.*—Quantity: Approximately 8 petals and 6 petaloids, of varying shape, per flower. Arrangement: Imbricate. Shape: Obovate. Apex: Obtuse. Base: Attenuate. Margin: Entire. Texture of upper and lower surface: Glabrous. Upper petal length: Approximately 2.4 cm. Upper petal width: Approximately 1.6 cm. Lower petal length: Approximately 2.2 cm. Lower petal width: Approximately 1.6 cm. Color of upper surface of fully open upper petals and petaloids: 58B with venation of 50B. Color of upper surface of fully open lower petals and petaloids: 58B. Color of lower surface of fully open upper petals and petaloids: 52A with venation of 50B. Color of lower surface of fully open of lower petals and petaloids: 55B.

*Pedicel.*—Strength: Strong. Angle: Acute. Length: Approximately 3.6 cm. Diameter: Approximately 1.2 mm. Texture: Soft, short dense hair, glandular. Color: 144A with glands of 28B.

*Calyx.*—Formed by 5 sepals. Sepal shape: Lanceolate. Sepal apex: Acuminate. Sepal base: Truncate. Sepal margin: Entire. Length of largest sepal: 1.1 cm. Width of largest sepal: 3.7 mm. Length of smallest sepal: 0.9 cm. Width of smallest sepal: 1.3 mm. Texture of both upper surface (inner) and lower surface(outer): Moderately glandular. Gland color:

Translucent. Sepal color: Upper and lower surface: 144A.

*Reproductive organs.*—Androecium: Filament quantity: Approximately 11. Filament color: N155B. Quantity of fertile anthers: Approximately 8. Anther length: Approximately 1.7 mm. Anther color: 183C. Pollen amount: Abundant. Pollen color 167A. Gynoecium: Pistil quantity: One per flower. Pistil length: Approximately 9.6 mm. Stigma shape: 5 pointed star. Stigma length: 2.2 mm. Stigma color: 185B. Style length: 2.4 mm. Style color: 185D. Ovary length: 5 mm. Ovary diameter: 5 mm. Ovary texture: Sericeous. Ovary color: 143A.

Seed and fruit production: Neither seed nor fruit production has been observed.

Disease and pest resistance: Resistance to pathogens and pests common to *geraniums* has not been observed.

What is claimed is:

1. A new and distinct cultivar of *Geranium* plant named 'Balfanimfro', substantially as herein shown and described.

* * * * *